United States Patent
Wochnowski et al.

[11] Patent Number: 5,086,279
[45] Date of Patent: Feb. 4, 1992

[54] METHOD OF AND APPARATUS FOR MEASURING THE MOISTURE CONTENT OF FIBROUS MATERIALS

[75] Inventors: Waldemar Wochnowski, Hamburg-Meiendorf; Heiko Niehues, Hamburg, both of Fed. Rep. of Germany

[73] Assignee: Körber AG, Hamburg, Fed. Rep. of Germany

[21] Appl. No.: 484,934

[22] Filed: Feb. 23, 1990

[30] Foreign Application Priority Data

Feb. 24, 1989 [DE] Fed. Rep. of Germany ....... 3905658

[51] Int. Cl.$^5$ ..................... G01R 27/04; G01N 22/04
[52] U.S. Cl. .................. 324/637; 324/640; 324/643; 324/647; 324/667
[58] Field of Search ............. 324/637, 639, 640, 642, 324/643, 641, 647, 664, 665, 667, 668, 683

[56] References Cited

U.S. PATENT DOCUMENTS

| | | | |
|---|---|---|---|
| 3,693,079 | 9/1972 | Walker | 324/640 X |
| 4,052,666 | 10/1977 | Fletcher et al. | 324/643 |
| 4,168,466 | 9/1979 | Boldt | 324/664 |
| 4,297,874 | 11/1981 | Sasaki | 324/640 X |
| 4,634,963 | 1/1987 | Lunden | 324/639 X |
| 4,675,595 | 6/1987 | Hane | 324/640 |
| 4,729,386 | 3/1988 | Heitmann | 131/84.1 |
| 4,789,820 | 12/1988 | Parrent, Jr. et al. | 324/643 X |

Primary Examiner—Jack B. Harvey
Attorney, Agent, or Firm—Peter K. Kontler

[57] ABSTRACT

A hygroscopic commodity, such as a continuous stream of shredded tobacco, is transported past one or more sources of electrical energy and past one or more monitoring devices. One of the sources can expose the stream to the electric field of a capacitor in a high frequency oscillator circuit, and the other source can expose the stream to infrared waves or microwaves. The moisture in the stream influences the phase and/or the damping of oscillations of the electrical energy, and the monitoring device of devices ascertain the changes of such characteristics of the electrical energy and transmit corresponding signals to a processing circuit which processes the signals into moisture signals. The processing circuit can generate first quotient signals which are indicative of phase shift and damping of oscillations of electrical energy which has penetrated the stream, and second quotient signals denoting the phase shift and damping of waves which are reflected by the stream, and such first and second quotient signals are or can be averaged for processing into moisture signals. The moisture signals are not dependent upon the chemical and/or biological properties and/or upon the composition of the monitored commodity.

39 Claims, 1 Drawing Sheet

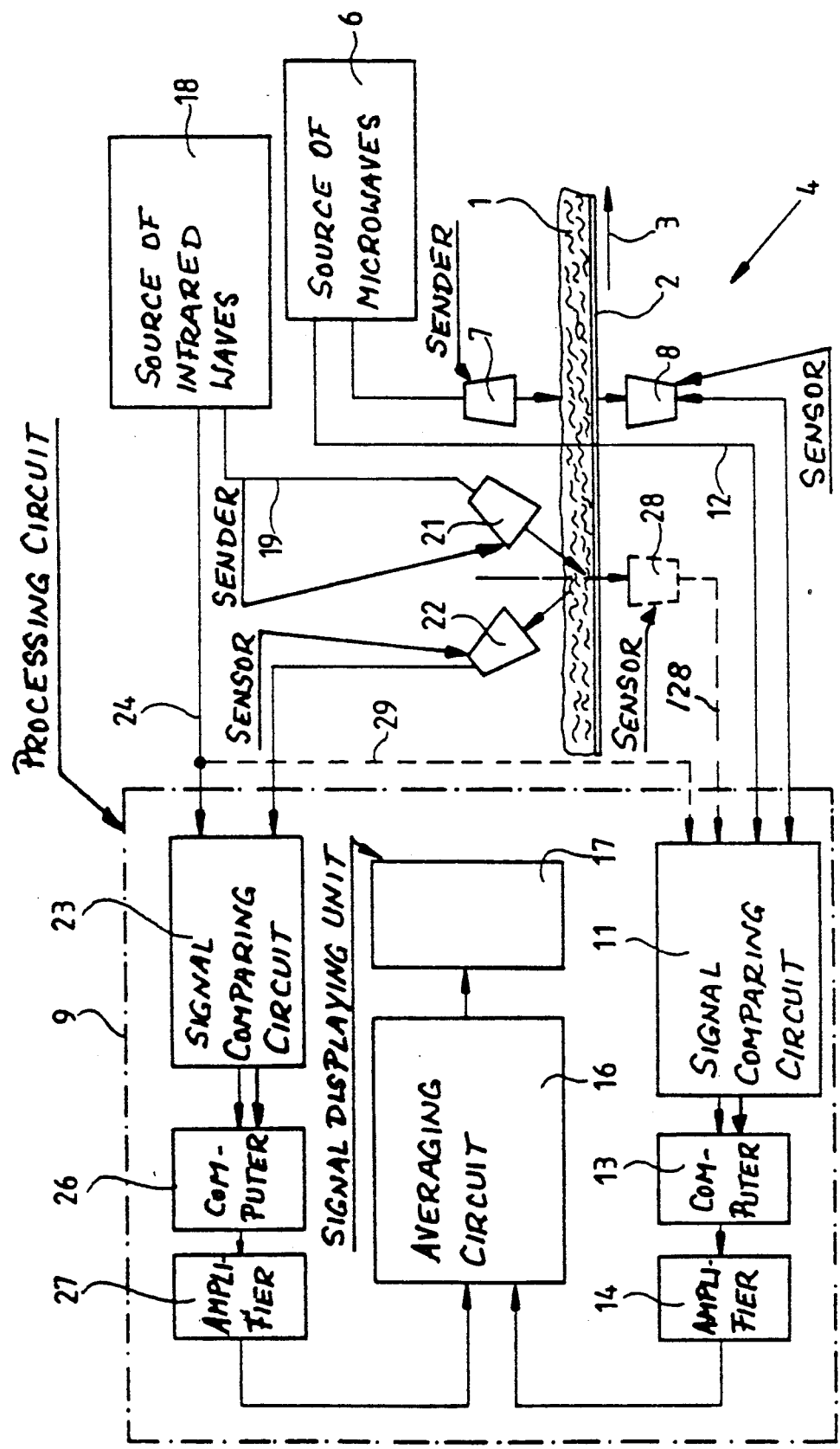

METHOD OF AND APPARATUS FOR MEASURING THE MOISTURE CONTENT OF FIBROUS MATERIALS

BACKGROUND OF THE INVENTION

The invention relates to a method of and to an apparatus for ascertaining or measuring the moisture content of certain commodities such as shredded tobacco, wood, foodstuffs and other hygroscopic materials.

The moisture content of certain hygroscopic materials plays an important role during making, processing and/or storage of such commodities. For example, the moisture content of tobacco shreds which are to be draped into cigarette paper or other wrapping material, or the moisture content of tobacco leaves which are to be converted into shreds, is normally maintained within a predetermined range. The same holds true for the making, processing and/or storage of wood, many types of foodstuffs and numerous other hygroscopic commodities. Therefore, it is customary to employ moisture measuring or detecting apparatus which are put to continuous use during making, processing and/or storage of the aforediscussed and/or other hygroscopic commodities. Heretofore known moisture measuring apparatus are quite reliable as long as the monitored commodities exhibit at least substantially uniform (homogeneous) chemical and biological properties. However, if the biological and/or chemical properties of the monitored commodities vary, or if the composition of the commodities changes, the results of measurements are no longer reliable and, in fact, can denote values which deviate considerably from the actual moisture content. Due to such dependency of conventional moisture measuring apparatus upon the "blend" of the hygroscopic commodities, their utility is rather limited and, therefore, it is often necessary to employ a wide variety of moisture measuring apparatus each of which can be put to use only under certain specific circumstances.

OBJECTS OF THE INVENTION

An object of the invention is to provide a novel and improved method of measuring the moisture content of shredded tobacco and/or other hygroscopic commodities in such a way that variations of the blend of monitored commodities cannot influence or cannot appreciably influence the reliability of measurements.

Another object of the invention is to provide a novel and improved apparatus for the practice of the above outlined method.

A further object of the invention is to provide an apparatus which is more versatile than heretofore known apparatus and is less affected by changes of consistency and chemical and/or biological properties of monitored commodities than conventional apparatus.

An additional object of the invention is to provide a novel and improved apparatus for measuring the moisture content of tobacco in a rod making machine.

Still another object of the invention is to provide a method which renders it possible to take into consideration a plurality of different parameters of the monitoring medium to thus enhance the accuracy and reliability of measurements of the moisture content.

A further object of the invention is to provide novel and improved signal processing means for use in the above outlined apparatus and in connection with the above outlined method.

SUMMARY OF THE INVENTION

One feature of the present invention resides in the provision of a method of measuring the moisture content of a commodity, such as tobacco. The method comprises the steps of exposing the commodity (e.g., a continuous stream of comminuted tobacco leaves on a driven belt conveyor in a cigarette making machine) to electrical energy having at least one characteristic which is influenced by moisture so that the influencing of the at least one characteristic of energy that penetrates the commodity by moisture in the commodity is indicative of the moisture content of the commodity, monitoring the energy which has penetrated the commodity and generating first signals denoting the at least one (influenced) characteristic of monitored electrical energy, and processing the first signals into further signals (hereinafter called moisture signals) which denote the moisture content of the commodity.

The at-least one characteristic can constitute the extent of oscillations of electrical energy, and such oscillations are damped by moisture in the commodity. Thus, the first signals are then indicative of the extent of damping of oscillations of electrical energy as a result of penetration of energy into the commodity.

The method can further comprise the steps of exposing the commodity to electromagnetic waves which are reflected by the commodity and the oscillations of which are damped by moisture in the commodity, monitoring the reflected waves, and generating second signals denoting the extent of damping of reflected waves. The processing step then comprises processing the first and second signals into moisture signals. Such processing step can comprise averaging the first and second signals and utilizing the averaged first and second signals for the generation of moisture signals.

The phase of electrical energy and of electromagnetic waves is influenced by moisture (i.e., such phase is a second characteristic which can be relied upon for determination of the moisture content) because the moisture in the commodity induces a phase shift. Therefore, the method can further comprise the steps of monitoring the energy which has penetrated the commodity and generating third signals which denote the phase shift of such electrical energy, monitoring the reflected electromagnetic waves and generating fourth signals which denote the phase shift of reflected electromagnetic waves. The processing step then preferably comprises processing the third and fourth signals into moisture signals, i.e., influencing the generation of moisture signals as a function of the third and/or fourth signals. The arrangement is or can be such that the processing step comprises converting the first and third signals into first quotient signals, converting the second and fourth signals into second quotient signals, and converting the first and second quotient signals into moisture signals. The step of converting the first and second quotient signals can include averaging the first and second quotient signals.

The method can also comprise the step of correcting or modifying at least one of the first, second, third and fourth signals with one or more empirically ascertained correction factors prior to the averaging step.

The electromagnetic waves can constitute microwaves, infrared waves or the electric field of a capacitor in a high frequency oscillator circuit. The same holds true for the electrical energy, i.e., such energy can consist of microwaves, infrared waves or of the electric field of the aforementioned capacitor.

Another feature of the invention resides in the provision of an apparatus for measuring the moisture content of a commodity, such as tobacco. The apparatus comprises a source of electrical energy having at least one characteristic which is influenced by moisture. The source includes means for exposing the commodity to electrical energy so that the energy penetrates into and its at least one characteristic is influenced by moisture in the commodity and is thus indicative of the moisture content of the commodity. The apparatus further comprises means for monitoring the energy which has penetrated the commodity, and the monitoring means includes means for generating first signals denoting the at least one (influenced) characteristic of monitored energy. The apparatus further comprises means for processing the first signals into moisture signals denoting the moisture content of the commodity. The at least one characteristic of energy to which the commodity is exposed can constitute the extent of oscillations of the energy, and such oscillations are damped by moisture in the commodity. The first signals are then indicative of the extent of damping of oscillations of energy as a result of penetration into the commodity. The processing means then comprises means for comparing the first signals with signals denoting undamped oscillations of the energy.

The apparatus can further comprise a source of electromagnetic waves, and such source can include means for exposing the commodity to electromagnetic waves so that the waves are reflected by the commodity and their oscillations are damped by moisture in the commodity. This apparatus further comprises means for monitoring the reflected waves and such monitoring means includes means for generating second signals which denote the extent of damping of reflected waves. The processing means of the just outlined apparatus includes means for processing the first and second signals into moisture signals. The means for processing the first and second signals can include means for averaging the first and the corresponding second signals and for utilizing the averaged signals for the generation of or as moisture signals.

The phase of the electrical energy and of the electromagnetic waves is influenced by moisture in such a way that moisture in the commodity induces a phase shift. Therefore, the processing means can further comprise means for generating third signals which denote the phase shift of electrical energy, means for generating fourth signals which denote the phase shift of reflected electromagnetic waves, and means for processing the third and fourth signals into moisture signals. The processing means can further comprise means for converting the first and third signals into first quotient signals, and means for converting the second and fourth signals into second quotient signals. The first and second quotient signals are then processed into moisture signals. The means for processing the first and second quotient signals can comprise means for averaging the quotient signals.

The processing means can further comprise means for correcting at least one of the first, second, third and fourth signals with an empirically ascertained correction factor prior to averaging of the quotient signals.

At least one of the sources can constitute a source of microwaves or a source of infrared waves. Alternatively, at least one of the sources can include a high frequency oscillator circuit having a capacitor which establishes an electric field and constitutes the exposing means of the respective source.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawing.

BRIEF DESCRIPTION OF THE DRAWING

The single FIGURE of the drawing is a schematic elevational view of an apparatus which embodies one form of the invention and wherein the commodity is a stream of shredded tobacco which is exposed to two different or identical electrical energies.

DESCRIPTION OF PREFERRED EMBODIMENTS

The drawing shows one reach of an endless flexible driven belt conveyor 2 which transports a continuous stream 1 of shredded tobacco in the direction of arrow 3. The stream 1 is transported in a cigarette rod making machine and is about to be trimmed (equalized) or draped into a web of cigarette paper or other suitable wrapping material. Reference may be had, for example, to commonly owned U.S. Pat. No. 4,729,386 granted Mar. 8, 1988 to Uwe Heitmann for "Apparatus for making cigarettes with dense ends." The purpose of the improved apparatus 4 is to continuously measure and indicate the moisture content of tobacco shreds which form the stream 1. The results of measurements can be displayed at 17 and/or used to alter the moisture content if the measured moisture content departs from the desired or optimum content. It is to be understood that a stream of shredded tobacco is but one of numerous commodities the moisture content of which can be ascertained in accordance with the method of and/or with the apparatus 4 of the present invention. For example, the apparatus 4 can be used to monitor the moisture content of a stream of tobacco leaves which are about to be shredded, to monitor the moisture content of wood, to monitor the moisture content of textile fibers, to monitor the moisture content of foodstuffs and/or to monitor the moisture content of other hygroscopic commodities during making and/or processing of such commodities.

The apparatus 4 exposes successive increments of the advancing stream 1 to electrical energy whereby at least one characteristic of the energy is influenced by moisture in the stream, and the apparatus ascertains changes of such at least one characteristic for the purposes of generating a moisture signal (namely a signal which is indicative of the moisture content of tobacco shreds) which is displayed at 17 and/or is used to alter the moisture content of tobacco shreds if the extent to which the monitored moisture content departs from the desired moisture content warrants a change.

The apparatus 4 comprises a first source 6 of electrical energy having means (7) for exposing successive increments of the stream 1 on the conveyor 2 to such energy in a predetermined portion of the path which is defined by the conveyor 2. The energy source 6 is a microwave generator and the exposing means 7 includes or constitutes a sender of microwaves. The orientation of the sender 7 with reference to the conveyor 2 is such that at least some of the microwaves penetrate through the stream 1 and can be detected by a receiver or sensor 8 which generates first signals denoting the extent of damping of oscillations of microwaves that have penetrated the stream and have reached the receiver 8. The output of the receiver 8 is connected with one input of a signal processing circuit 9 which processes the first signals into moisture signals. To this end, the processing circuit 9 comprises a signal comparing circuit 11 which receives first signals from the output of the receiver 8 and which further receives additional signals directly from the source 6 or its sender 7 via conductor 12. The additional signals are indicative of oscillations of electrical energy which was not influenced by moisture in the stream 1. The circuit 11 compares the amplitudes of the first signals with those of signals which are transmitted via conductor 12. The signals at the output of the comparing circuit 11 are indicative of the extent of damping of oscillations of electrical energy by moisture in the stream 1.

Moisture in the stream 1 also influences the phase of electrical energy by causing a phase shift. The circuit 11 compares the phase of signals from the receiver 8 with the phase of signals which are transmitted by the conductor 12 and generates (third) signals which are indicative of the moisture-induced phase shift. As can be seen in the drawing, the circuit 11 has two outputs, namely one for the first signals and one for the third signals. Such signals are transmitted to a computer unit 13 which converts the first and third signals into first quotient signals and transmits such quotient signals to a further computer unit 14. Signals which are transmitted by the computer unit 13 denote the moisture content of tobacco shreds in the stream 1 and are independent of the mass and density of the stream. However, such quotient signals are still dependent upon the blend of shreds in the stream, i.e., they are influenced by the biological and/or chemical characteristics as well as upon the composition of the stream. The computer unit 14 can include or constitute an amplifier the output of which is connected with a further computer unit 16 having an output connected with the means 17 for displaying moisture signals.

The illustrated apparatus 4 further comprises a second source 18 of electrical energy, namely a source of electromagnetic waves. The illustrated second energy source 18 is a source of infrared waves and includes or is connected with a sender 21 (see the conductor 19) which emits infrared waves in such direction that emitted waves are reflected by the stream 1 and impinge upon an infrared wave sensor or detector 22. The latter generates (second) signals which are indicative of the extent to which the infrared waves were influenced by moisture in the respective increments of the stream 1, namely the extent to which the oscillations of the infrared waves are damped by moisture. The second signals are transmitted to one input of a signal comparing circuit 23 forming part of the processing circuit 9 and having a second input connected directly with the source 18 or with the sender 21 via conductor 24. The circuit 23 compares the second signals with signals which are indicative of electrical energy that is not influenced by the moisture in the stream 1, and the circuit 23 transmits signals which are indicative of the moisture content of the stream 1. Such signals denote the extent of damping of oscillations of waves which are emitted by the sender 21.

The phase of electromagnetic waves which are directed against the stream 1 by the sender 21 is also influenced by moisture in the stream. Therefore, the circuit 23 further serves to ascertain the phase shift which is attributable to moisture in the shreds of the stream 1 and has two outputs one of which emits (second) signals denoting the extent of damping of oscillation of infrared waves and (fourth) signals denoting the phase shift which is attributable to moisture in the stream 1. The two outputs of the signal comparing circuit 23 are connected to a computer unit 26 which ascertains the quotient of the second and fourth signals and transmits (second) quotient signals to a computer unit 27 which constitutes or includes an amplifier and is connected with a second input of the circuit 16.

The circuit 16 performs the function of an averaging circuit which ascertains the arithmetic average value of quotient signals transmitted by the computer units 13, 26 and amplified by the respective computer units 14, 27. The thus obtained averaged moisture signals are transmitted to the displaying means 17. An advantage of the circuit 16 is that the moisture signal which is obtained from the averaged first and second quotient signals is independent of the mass and density as well as of the blend (i.e., chemical and/or biological properties as well as the surface configuration and composition) of the monitored commodity.

The amplifier 14 further serves as a means for conforming the quotient signals from the computer unit 13 to quotient signals from the computer unit 26. To this end, the amplifier 14 compares the quotient signals from the computer unit 14 with an empirically ascertained correction factor. Such correction factor can be ascertained on the basis of determination of first quotient signals for a particular commodity in dependency on a variety of known moisture contents. These first quotient signals (obtained as a result of monitoring of electrical energy which has penetrated through and electrical energy (from the same source) which did not penetrate into and/or through a commodity having a known moisture content) are used to set up a first straight valuation or calibration curve. The procedure is repeated in connection with the same commodity but having different known moisture contents to determine at least one second calibration curve. The just described determinations of calibration curves can be carried out in a laboratory. The next step involves at least substantial overlapping of the first and second calibration curves on the basis of transformation. The thus obtained mathematical values are stored in the memory of the amplifier 14 as empirically ascertained correction factors. All following measurements of moisture content of a commodity involve (when necessary) a correction of first quotient signals from the computer unit 13 with the corresponding correction factors.

The amplifier 27 also serves for storage of correction factors which are used to correct second quotient signals from the computer unit 26. The correction factors which are stored in the amplifier 27 are obtained as a result of determination of changes of the extent of damping and phase shift of waves which were reflected by commodities having known moisture contents.

As already described above, the source 6 is a source of microwaves and the source 18 is a source of infrared waves. However, it is equally within the purview of the invention to employ a source of microwaves which are reflected by the commodity and to employ a source of infrared waves which are caused to penetrate into and through the commodity. The drawing shows by broken lines an infrared sensor 28 which is positioned to generate signals denoting the waves which have penetrated through the stream 1. The corresponding signals are transmitted to the comparing circuit 11 by a conductor 128, and a further conductor 29 branches from the conductor 24 to transmit to the circuit 11 signals the oscillations of which were not influenced by moisture in the stream 1. This enables the circuit 11 to generate signals denoting the extent to which the oscillation of signals from 21 to 28 was damped by the stream 1.

It is further possible to replace the source 6 and/or the source 18 with a high frequency oscillator circuit having a capacitor which establishes an electric field to which the stream 1 is exposed. The capacitor can at least partially surround the path for the stream 1. The damping of oscillations of high frequency electrical energy is ascertained by a suitable detector in conjunction with a comparing circuit (such as the circuit 11) for the generation of corresponding (first) signals which are processed at 13, 14 and 16 in the aforedescribed manner.

The drawing shows a processing circuit 9 which comprises a plurality of discrete computer units, circuits, amplifiers and/or other components. Such illustration of the processing unit 9 has been chosen for convenience of description of various processing or evaluating steps. In actual practice, the functions of the components 11, 13, 14, 16, 23, 26 and 27 can be carried out by a central computer or processor which performs the aforedescribed functions in accordance with a predetermined program.

An important advantage of the improved method and apparatus is that moisture signals which are transmitted by the circuit 16 are not influenced by the mass and/or density of the stream 1 even though the apparatus 4 need not comprise any means for ascertaining the mass and/or the density of the monitored commodity. This is due to the fact that the apparatus generates and processes (third and fourth) signals which are indicative of phase shift of the respective energy under the influence of moisture in the monitored commodity and that such (third and fourth) signals are processed with the respective (first and second) signals to form first and second quotient signals. Averaging of the first and second quotient signals in the circuit 16 ensures that the moisture signals are independent of the mass and density as well as blend (composition and chemical and/or biological properties) of the commodity.

The aforedescribed correction of first and second quotient signals in the amplifiers 14 and 27 constitutes the presently preferred mode of processing the first, second, third and fourth signals. However, it is equally possible to correct only the first, only the second, only the third, only the fourth, only the first and third or only the second and fourth signals prior to the averaging step at 16.

The improved apparatus can be used for determination of the moisture content of a stationary (stagnant) or conveyed (moving) commodity. Since the signals at the output of the averaging circuit 16 are indicative of the moisture content of monitored commodity and are not dependent upon the mass, density and/or blend of the commodity, the improved apparatus is much more versatile than heretofore known moisture measuring apparatus. One of the presently preferred utilizations of the apparatus is in connection with the processing of tobacco, e.g., for the measurement of moisture content of tobacco shreds which are to be converted into the filler of a continuous cigarette rod. It is highly desirable and advantageous to maintain the moisture content of tobacco shreds in a cigarette rod making machine within a predetermined narrow range independently of the mass, density and/or blend. It is also possible to employ the apparatus for determination of the moisture content of tobacco leaves which are about to be converted into shreds.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A method of measuring the moisture content of a commodity, comprising the steps of exposing the commodity to oscillating electrical energy the oscillations of which are influenced by moisture so that the influencing of the oscillations of energy that penetrates the commodity is indicative of the moisture content of the commodity; monitoring the energy that has penetrated the commodity and generating first signals denoting the extent of oscillations of monitored energy, said first signals being indicative of the extent of damping of oscillations of the energy as a result of penetration into the commodity; exposing the commodity to electromagnetic waves which are reflected by the commodity and the oscillations of which are damped by moisture in the commodity; generating second signals denoting the extent of damping of reflected waves; averaging each first signal with a second signal; and utilizing the thus obtained averaged signals for the generation of moisture signals.

2. The method of claim 1 wherein the phase of electrical energy and of electromagnetic waves is influenced by moisture and the moisture in the commodity induces a phase shift, and further comprising the steps of generating third signals denoting the phase shift of electrical energy and generating fourth signals denoting the phase shift of reflected electromagnetic waves, said utilizing step further comprising processing said third and fourth signals into moisture signals.

3. The method of claim 2, wherein said utilizing step comprises converting said first signals and said third signals into first quotient signals, converting said second signals and said fourth signals into second quotient signals, and converting said first and second quotient signals into said moisture signals.

4. The method of claim 3, wherein said step of converting said first and second quotient signals includes averaging each first quotient signal with a second quotient signal.

5. The method of claim 4, further comprising the step of correcting at least one of said first, second, third and fourth signals with an empirically ascertained correction factor prior to said averaging step.

6. The method of claim 1, wherein said electromagnetic waves are microwaves.

7. The method of claim 1, wherein said electromagnetic waves are infrared waves.

8. The method of claim 1, wherein said electrical energy consists of microwaves.

9. The method of claim 1, wherein said electrical energy consists of infrared waves.

10. The method of claim 1, wherein said electrical energy is the electric field of a capacitor in a high frequency oscillator circuit.

11. Apparatus for measuring the moisture content of a commodity, comprising a source of oscillating electrical energy having at least one characteristic which is influenced by moisture, said source having means for exposing the commodity to electrical energy so that the energy penetrates into the commodity and the extent of oscillations is influenced by moisture in the commodity and is indicative of moisture content of the commodity; means for monitoring the energy that has penetrated the commodity including means for generating first signals denoting the extent of damping of the monitored energy; a source of electromagnetic waves including means for exposing the commodity to electromagnetic waves so that the waves are reflected by the commodity and their oscillations are damped by moisture in the commodity; means for monitoring the reflected waves including means for generating second signals denoting the extent of damping of reflected waves; and means for processing said first and second signals including measn for averaging each first signal with a second signal and utilizing the thus obtained averaged signals for the generation of moisture signals.

12. The apparatus of claim 11, wherein the oscillations are damped by moisture in the commodity, said first signals being indicative of the extent of damping of oscillations of energy as a result of penetration into the commodity, said processing means further including means for comparing said first signals with signals denoting undamped oscillations of the energy.

13. The apparatus of claim 11, wherein the phase of electrical energy and of electromagnetic waves is influenced by moisture and the moisture in the commodity induces a phase shift, said processing means including means for generating third signals denoting the phase shift of electrical energy, means for generating fourth signals denoting the phase shift of reflected electromagnetic waves, and means for processing said third and fourth signals into moisture signals.

14. The apparatus of claim 13, wherein said processing means further comprises means for converting said first and third signals into first quotient signals, means for converting said second and fourth signals into second quotient signals, and means for processing said first and second quotient signals into moisture signals.

15. The apparatus of claim 14, wherein said means for processing said first and second quotient signals comprises means for averaging each first quotient signal with a second quotient signal.

16. The apparatus of claim 15, wherein said processing means further comprises means for correcting at least one of said first, second, third and fourth signals with an empirically ascertained correction factor prior to averaging of said quotient signals.

17. The apparatus of claim 11, wherein at least one of said sources is a source of microwaves.

18. The apparatus of claim 11, wherein at least one of said sources is a source of infrared waves.

19. The apparatus of claim 11, wherein said source of electrical energy is a source of microwaves.

20. The apparatus of claim 11, wherein said source of electrical energy is a source of infrared waves.

21. The apparatus of claim 11, wherein said source of electrical energy includes a high frequency oscillator circuit having a capacitor which establishes an electric field, said capacitor constituting said exposing means of said source of electrical energy.

22. The apparatus of claim 11, further comprising means for conveying the commodity past said means for exposing the commodity to electrical energy and past said means for monitoring the energy.

23. A method of measuring the moisture content of a commodity, comprising the steps of exposing the commodity to oscillating electrical energy the oscillations of which are influenced by moisture so that the influencing of the oscillations of energy that penetrates the commodity is indicative of the moisture content of the commodity; monitoring the energy that has penetrated the commodity and generating first signals denoting the extent of oscillations of monitored energy, said first signals being indicative of the extent of damping of oscillations of the energy as a result of penetration into the commodity; exposing the commodity to electromagnetic waves which are reflected by the commodity and the oscillations of which are damped by moisture in the commodity; monitoring the reflected waves; generating second signals denoting the extent of damping of the reflected waves; generating third signals denoting the phase shift of electrical energy; generating fourth signals denoting the phase shift of the reflected electromagnetic waves; converting said first signals and said third signals into first quotient signals; converting said second signals and said fourth signals into second quotient signals; and converting said first and second quotient signals into moisture signals.

24. The method of claim 23, wherein said step of converting said first and second quotient signals includes averaging the first and second quotient signals.

25. The method of claim 24, further comprising the step of correcting at least one of said first, second, third and fourth signals with an empirically ascertained correction factor prior to said averaging step.

26. The method of claim 23, wherein said electromagnetic waves are microwaves.

27. The method of claim 23, wherein said electromagnetic waves are infrared waves.

28. The method of claim 23, wherein said electrical energy consists of microwaves.

29. The method of claim 1, wherein said electrical energy consists of infrared waves.

30. The method of claim 23, wherein said electrical energy is the electrical field of a capacitor in a high frequency oscillator circuit.

31. Apparatus for measuring the moisture content of a commodity, comprising a source of oscillating electrical energy having at lest one characteristic which is influenced by moisture, said source having means for exposing the commodity to electrical energy so that the energy penetrates into the commodity and the extent of oscillations is influenced by moisture in the commodity and is indicative of moisture content of the commodity; means for monitoring the energy that has penetrated the commodity including means for generating first signals denoting the extent of damping of oscillations of the monitored energy; a source of electromagnetic waves including means for exposing the commodity to electromagnetic waves so that the waves are reflected by the commodity and their oscillations are damped by moisture in the commodity; means for monitoring the reflected waves including means for generating second signals denoting the extent of damping of reflected waves; and processing means including means for generating third signals denoting the phase shift of the electrical energy, means for generating fourth signals denoting the phase shift of the reflected electromagnetic waves, means for converting said first and third signals into first quotient signals, means for converting said second and fourth signals into second quotient signals, and means for processing said first and second quotient signals into moisture signals.

32. The apparatus of claim 31, wherein said means for processing said first and second quotient signals, comprises means for averaging said quotient signals.

33. The apparatus of claim 32, wherein said processing means further comprises means for correcting at least one of said first, second, third and fourth signals with an empirically ascertained correction factor prior to averaging of said quotient signals.

34. The apparatus of claim 31, wherein at least one of said sources is a source of microwaves.

35. The apparatus of claim 31, wherein at least one of said sources is a source of infrared waves.

36. The apparatus of claim 31, wherein said source of electrical energy is a source of microwaves.

37. The apparatus of claim 31, wherein said source of electrical energy is a source of infrared waves.

38. The apparatus of claim 31, wherein said source of electrical energy includes a high frequency oscillator circuit having a capacitor which establishes an electric field, said capacitor constituting said exposing means of said source of electrical energy.

39. The apparatus of claim 31, further comprising means for conveying the commodity past said means for exposing the commodity to electrical energy and past said means for monitoring the energy.

* * * * *